US00PP21758P2

(12) United States Plant Patent
Korlipara

(10) Patent No.: US PP21,758 P2
(45) Date of Patent: Mar. 1, 2011

(54) ***COREOPSIS* PLANT NAMED 'RUBY FROST'**
(50) Latin Name: ***Coreopsis* sp.**
Varietal Denomination: Ruby Frost

(75) Inventor: Harini Korlipara, Canby, OR (US)
(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/592,188

(22) Filed: Nov. 20, 2009

(51) Int. Cl.
*A01H 5/00* (2006.01)

(52) U.S. Cl. ..... Plt./417
(58) Field of Classification Search ..... Plt./417

See application file for complete search history.

*Primary Examiner*—June Hwu
(74) *Attorney, Agent, or Firm*—Klarquist Sparkman, LLP

(57) ABSTRACT

A new and distinct *Coreopsis* plant named 'Ruby Frost' characterized by large, daisy-type flowers that grow to 5.5 cm in diameter, white-edged red purple flowers, grass green foliage on short stems, flowering for the whole summer, and a dense, mounding habit.

1 Drawing Sheet

Botanical denomination: *Coreopsis* sp.
Variety designation: 'Ruby Frost'.
Parentage: (*Coreopsis* 'Rum Punch'×*Coreopsis lanceolata* 'Sonnenkind').

BACKGROUND OF THE INVENTION

The present invention relates to a new and distinct hybrid of *Coreopsis* and given the cultivar name 'Ruby Frost'. *Coreopsis* is in the family Asteraceae. This new cultivar originated from a controlled cross of *Coreopsis* 'Rum Punch' (U.S. Plant Pat. No. 18,889), as the seed parent and *Coreopsis lanceolata* 'Sonnenkind', an unpatented plant, as the pollen parent. Compared to the seed parent, *Coreopsis* 'Rum Punch', the new hybrid has white-edged, red purple flowers rather than orange-rose flowers. Compared to the pollen parent, *Coreopsis lanceolata* 'Sonnenkind', the new hybrid has white-edged, red purple flowers rather than yellow orange. The closest known variety known to the breeder is 'Cranberry Ice' (U.S. Plant Pat. No. 19,470), the new hybrid is much more compact than 'Cranberry Ice'. The new hybrid has a clear white edged petal rather than the mottled white edged petal of 'Cranberry Ice'.

SUMMARY OF THE INVENTION

The following traits have been repeatedly observed and are determined to be the unique characteristics of the new variety. These characteristics in combination distinguish *Coreopsis* 'Ruby Frost' as a new and distinct cultivar:

1. large daisy-type flowers that grow to 5.5 cm in diameter,
2. white-edged red purple flowers
3. grass green foliage on short stems,
4. flowering for the whole summer, and
5. a dense, mounding habit.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

The photograph shows a one year old *Coreopsis* 'Ruby Frost' growing in the ground in the trial field in August in Canby, Oreg.

DETAILED PLANT DESCRIPTION

The following is a detailed description of the new *Coreopsis* cultivar based on observations of a 16-month-old specimen growing in the ground in full sun under typical outdoor conditions in the trial fields in July in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart, $5^{th}$ edition.

Plant:
- *Type.*—Herbaceous perennial.
- *Hardiness.*—USDA Zones 7 to 9.
- *Size.*—81 cm wide and 41 cm tall to top of inflorescences.
- *Form.*—Mound.
- *Vigor.*—Excellent.
- *Roots.*—Fibrous, stems root easily from stem cuttings.

Stem:
- *Type.*—Ascending.
- *Size.*—25 cm tall to where branches for flowering and 4 mm wide.
- *Number of stems from the crown.*—About 150.
- *Internode length.*—2 to 5 cm.
- *Surface.*—Sparsely pubescent.
- *Color.*—Yellow Green 137A.

Leaf:
- *Type.*—Pinnately compound.
- *Shape.*—Ovate.

*Lobing.*—3 to 5 pinnatifid, lobes linear, each lobe 1 to 2 mm wide and 20 to 36 mm long, except lowest leaves which have wider terminal lobes (5 mm), elliptic.

*Arrangement.*—Opposite.

*Size.*—Grows to 5 cm long and 2 cm wide.

*Margins.*—Entire.

*Petiole.*—Length 5 to 25 mm, width 0.5 to 1 mm, margins pubescent, Green 137A.

*Apex.*—Acute.

*Surface texture.*—Pubescent.

*Venation.*—Pinnate.

*Color.*—Top side Green 137A, bottom side Yellow Green 146A.

Inflorescence:

*Type.*—Long stalked terminal heads of daisy type inflorescences.

*Peduncle.*—12 cm tall, 1 mm wide, sparsely pubescent, Green 137A.

*Size.*—Grow to 5 cm wide and 10 mm deep.

*Immature.*—7 mm long and 7 mm wide, ovoid, glabrous, Greyed Purple 187A on very top with Greyed Yellow 161A below and Yellow Green 146A on bottom.

*Receptacle.*—Disc shaped, 5 mm wide and 2 mm deep, Yellow Green 146B.

*Phyllary.*—In two series; inner series broadly campanulate with 8 lobes, grows to 11 mm wide and 7 mm deep, each lobe ovate, entire, acute, glabrous on both sides, 7 mm long and 4 mm wide, on both sides top half Yellow 12B edged with Greyed Purple 187A, bottom half Green 137A; outer series stellate, with 8 lobes, grows to 7 mm wide and 2 mm deep, lobes ovate, entire, acute, 3 mm long and 2 mm wide, Green 137A on both sides with tips Greyed Purple 187A.

*Lastingness.*—Each inflorescence lasts about a week on the plant.

Florets:

*Type.*—Composite.

*Ray florets.*—8 in number with no pistil or stamen, obovate with the tip three lobed with lobes obtuse and notched and the central lobe the longest and most notched, entire on sides, grows to 26 mm long, 16 mm wide, glabrous; occasionally with one extra narrow limb from the base, linear, perpendicular to the main ray petal, 14 mm long and 1 mm wide; topside bottom ⅓ Purple N79A to middle color between Purple N79C and Red Purple 59A to lobes with Red Purple 69C; bottom side Orange White 159A on lobes darkening to a lower spot of Greyed Purple 187C.

*Disc.*—Conic, deeper with maturity, 10 mm wide and becoming 5 mm deep with maturity, Greyed Orange 166A before opening, after opening Orange 20A with a background of Greyed Purple 187A.

*Disc florets.*—With stamen and pistil, about 110 in number, 6 mm long and 1 mm wide, tubular; corolla 4.5 mm long, Greyed Purple 187A at the apex to Yellow 10B near base; pistil 1, ovary 1.5 mm long, Yellow Green 149D, style 5 mm long, extruding, with 2-branched stigma, stigma and style Orange 24A; stamen 5, anthers 2 mm long, Greyed Purple N187A, no pollen.

*Bloom period.*—June through September in Canby, Oreg.

*Fragrance.*—Light, Chrysanthemum-like.

*Seed.*—None produced.

*Fertility.*—Infertile.

Disease and pests: *Coreopsis* are susceptible to mildew and fungal spots. No resistance is known for this variety.

I claim:

1. A new and distinct *Coreopsis* plant as herein illustrated and described.

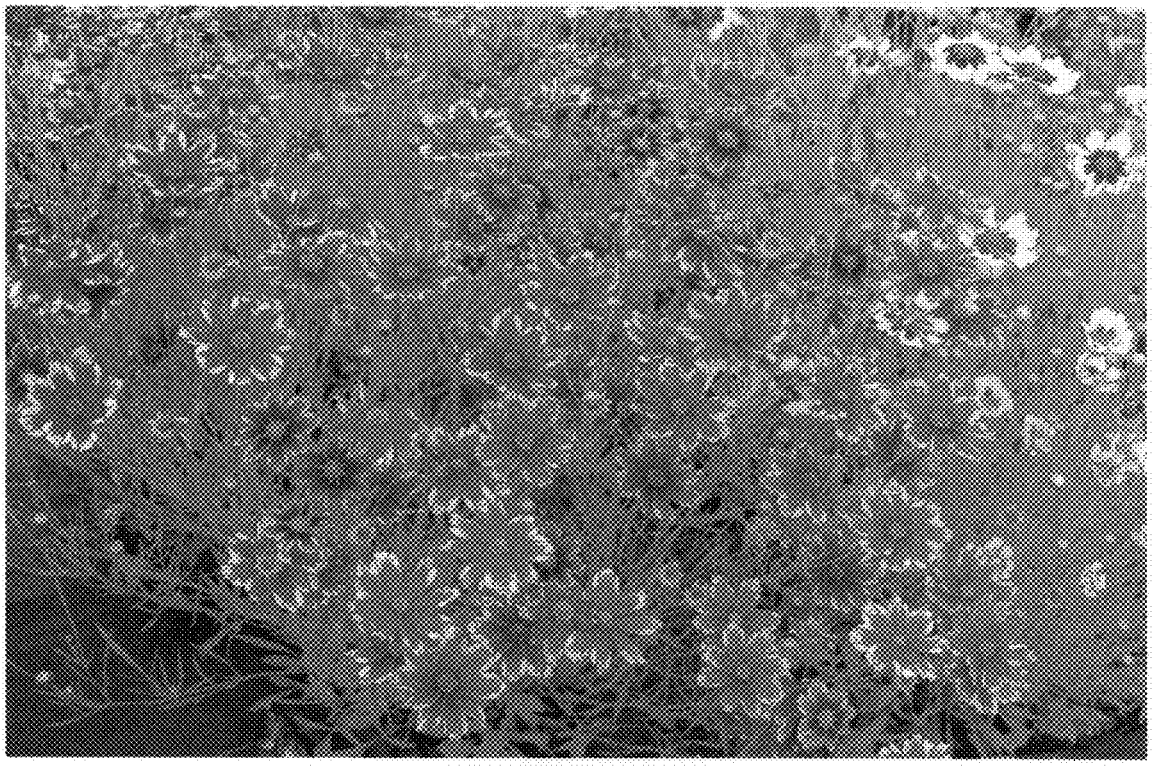

* * * * *